(12) United States Patent
Murugan et al.

(10) Patent No.: US 8,748,660 B2
(45) Date of Patent: Jun. 10, 2014

(54) PROCESS FOR THE SYNTHESIS OF ANTIEPILEPTIC DRUG LACOSAMIDE

(75) Inventors: Muthukrishnan Murugan, Pune (IN); Mohammad Mujahid, Pune (IN); Prashant Pramod Majumdar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/589,923

(22) Filed: Aug. 20, 2012

(65) Prior Publication Data
US 2014/0012044 A1    Jan. 9, 2014

(30) Foreign Application Priority Data
Jul. 9, 2012    (IN) .............................. 2112DEL2012

(51) Int. Cl.
*C07C 233/05*    (2006.01)
*C07C 231/08*    (2006.01)

(52) U.S. Cl.
USPC ......................................... 564/158; 564/155

(58) Field of Classification Search
USPC ................................................... 564/155, 158
See application file for complete search history.

(56) References Cited

U.S. PATENT DOCUMENTS

| RE38,551 E | 7/2004 | Kohn |
| 2009/0143472 A1 | 6/2009 | Madhra et al. |
| 2011/0130350 A1 | 6/2011 | Riedner et al. |
| 2011/0178092 A1* | 7/2011 | Ali et al. ................. 514/252.01 |
| 2012/0095251 A1* | 4/2012 | Wisdom et al. ................. 560/29 |

FOREIGN PATENT DOCUMENTS

| WO | WO2006/037574 | 4/2006 |
| WO | WO2011039781 | 4/2011 |
| WO | WO2011/095995 | 8/2011 |

* cited by examiner

*Primary Examiner* — Shailendra Kumar
(74) *Attorney, Agent, or Firm* — Ladas & Parry LLP

(57) ABSTRACT

The present invention relates to the improved and efficient process for the synthesis of antiepileptic drug Lacosamide in high enantiopurity (>98% ee) and better yield. More particularly, the present invention relates to improved and efficient, cost effective process for synthesis of desired (R) isomer of Lacosamide starting from commercially available (S)-benzyl glycidyl ether.

13 Claims, 2 Drawing Sheets

Scheme-1

Scheme-2

PROCESS FOR THE SYNTHESIS OF ANTIEPILEPTIC DRUG LACOSAMIDE

FIELD OF THE INVENTION

The present invention relates to improved and efficient process for the synthesis of antiepileptic drug, Lacosamide in high enantiopurity and yield.

More particularly, the present invention relates to improved and efficient, cost effective process for synthesis of desired (R) isomer of Lacosamide starting from commercially available (S)-benzyl glycidyl ether.

BACKGROUND AND PRIOR ART OF THE INVENTION

Lacosamide is the (R)-enantiomer of N-benzyl-2-acetamido-3-methoxypropionamide (FIG. 1) recently approved by FDA (October, 2008) as an add-on therapy for partial-onset seizures in adults with epilepsy. Epilepsy is a complex neurological disorder characterized by recurrent spontaneous seizures and it affects almost 50 million people worldwide. The life time prevalence of this disease is 1% and it affects individuals of all ages regardless of gender or socio-economic status. Further, epilepsy requires prolonged and sometimes lifelong drug therapy.

Although the mechanism of action of Lacosamide is not yet clearly understood, but it is believed that it enhances slow inactivation of voltage-gated Na+ channels and binds to dihydropyrimidinase-related protein 2 (CRMP 2), and thus controls the seizures. Due to this unique mode of action, it differs from other antiepileptic drugs (AEDs). Commercially, Lacosamide is prepared using a chiral pool approach starting from unnatural amino acid D-serine and its derivatives.

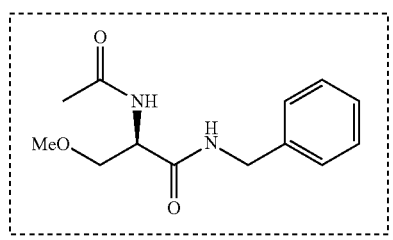

Lacosamide (Vimpat®)1

Lacosamide and its methods of preparation are disclosed in Reissue U.S. Pat. No. RE 38,551, involves reaction of protected and deprotected active groups (such as amino, hydroxyl and carboxylic group) of D-serine derivatives that subsequently yield lacosamide.

An alternative method for the preparation of Lacosamide is disclosed in PCT publication WO 2006/037574 which involves O-methylation of N-Boc-protected-D-serine ("Boc" refers to t-butoxycarbonyl) directly in one step by avoiding simultaneous formation of the methyl ester moiety. WO/2011/095995 also discloses an alternate process for preparation of lacosamide. Further, intermediate compounds such as D-serinamide derivatives and their use in the preparation of lacosamide are disclosed in US20090143472 and WO2011039781. References may be made to patent application US20110130350, wherein improved method for preparation of Lacosamide is disclosed, wherein the intermediate (R)-2-N-Boc-amino-3-methoxypropanoic acid is prepared from N-Boc-D-serine using phase transfer catalyst.

The existing processes for the synthesis of R-isomer of Lacosamide comprise unnatural amino acid D-serine or its derivatives as starting material which is costly.

Therefore, there is need for practical and highly enantioselective synthesis of R-isomer of lacosamide using readily available, cheap starting material other than D-serine and its derivatives.

In view of the above disadvantages, the present inventors have demonstrated improved and efficient new process for the synthesis of R-lacosamide starting from commercially available (S)-benzyl glycidyl ether. Further, (S)-benzyl glycidyl ether can easily be obtained from racemic benzyl glycidyl ether using Jacobsen's HKR (hydrolytic kinetic resolution) strategy. Therefore, the objective of the present invention is to provide efficient, cost-effective and improved process for the synthesis of R-lacosimide with high enantiopurity (>98% ee) starting from readily available starting material (S)-benzyl glycidyl ether.

OBJECTS OF THE INVENTION

Main object of the present invention is to provide efficient, cost-effective and improved process for the synthesis of R-Lacosamide with high enantiopurity (>98% ee) starting from readily available starting material (S)-benzyl glycidyl ether.

ABBREVIATIONS

TBAI: Tetrabutylammonium iodide
DPPA: Diphenylphosphoryl azide
DIAD: Diisopropyl azodicarboxylate
Ph$_3$P: Triphenyl phosphine
TEMPO: (2,2,6,6-Tetramethylpiperidin-1-yl)oxyl; or (2,2,6,6-tetramethylpiperidin-1-yl)oxidanyl
Boc: tert-Butoxy carbonyl
Fmoc: 9-fluorenylmethyloxycarbonyl
Tos: 4-Toluenesulfonyl chloride
Cbz: Carboxybenzyl
DCM: Dichloromethane
NMM: N-Methylmorpholine
THF: Tetrahydrofuran
(R): R-isomer or enantiomer
(S): S-isomer or enantiomer

SUMMARY OF THE INVENTION

Accordingly, present invention provides a process for synthesis of >98% ee enantio-pure Lacosamide (R)-1 from (S)-benzyl glycidyl ether and the said process comprising the steps of:

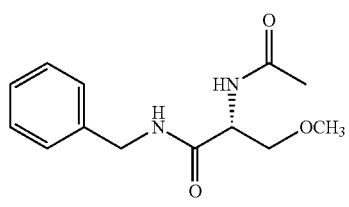

Lacosamide (R)-1 i. regioselective ring opening of compound (S)-benzyl glycidyl ether (S)-2 in presence of base and alcohol at temperature in the range of 0 to 60° C. for period in the range of 7 to 10 h to obtain corresponding sec-alcohol (S)-3;

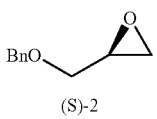 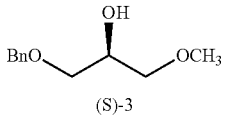

(S)-2                    (S)-3 ii. preparing azido derivative (R)-4 from sec-alcohol (S)-3 under Mitsunobu condition;

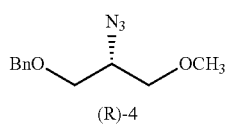

(R)-4 iii. catalytical hydrogenation, hydrogenolysis and concomitant protection of (R)-4 as obtained in step (ii) by using protecting group in solvent to obtain compound (S)-7;

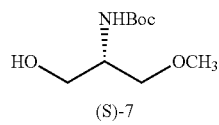

(S)-7 iv. oxidizing (S)-7 as obtained in step (iii) in presence of (2,2,6,6-Tetramethylpiperidin-1-yl)oxyl (TEMPO) and bleach in acetonitrile-phosphate buffer of pH in the range of 6.0 to 7.0 in solvent to obtain (R)-8;

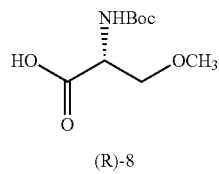 [SMILES: COC[C@@H](NC(=O)OC(C)(C)C)C(=O)O]

(R)-8 v. subsequent coupling of (R)-8 as obtained in step (iv) with benzyl amine using mixed anhydride method to obtain (R)-9;

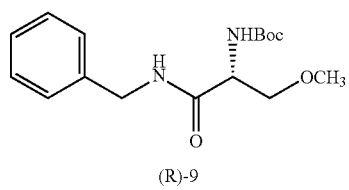 [SMILES: COC[C@@H](NC(=O)OC(C)(C)C)C(=O)NCc1ccccc1]

(R)-9 vi. deprotecting (R)-9 as obtained in step (iv) and (v) followed by N-acetylation in presence of acetylating agent, base and solvent to obtain Lacosamide (R)-1.

In an embodiment of the present invention, base is selected from the group consisting of metal hydrides, hydroxides, oxides, carbonates, bicarbonates, alkoxides, or primary and secondary amine, ammonia, alkyl amine; preferably NaOH, KOH, $Na_2CO_3$, $NaHCO_3$, $NaOCH_3$.

In another embodiment of the present invention, the alcohol is selected from the group consisting of (C1-C5) alcohol, branched alcohol, diol, triol, aryl alcohol; preferably, C1-C5-alcohols.

In yet another embodiment of the present invention, the temperature is maintained in the range between −20° C. to 60° C. preferably −20° to 40° C.

In yet another embodiment of the present invention, catalytic hydrogenation is carried out in presence of $H_2$ and catalyst selected from the group consisting of Pd/C, Pt/C, Raney Ni, Rh/C, Platinum oxide, $Pd(OH)_2/C$, Lithium aluminium hydride, ammonium formate or mixture thereof.

In yet another embodiment of the present invention, the protecting groups are selected from the group consisting of Boc, Cbz, Tos or Fmoc preferably Boc.

In still another embodiment of the present invention, temperature in the range of (−) 60 to (−) 90° C. preferably (−) 70 to (−) 80° C.

In yet another embodiment of the present invention, acetylating agent used is selected from the group consisting of acetic anhydride, acetyl chloride, acetic acid and mixture thereof or suitable derivatives thereof.

In yet another embodiment of the present invention, the base is selected from the group consisting of carbonates, bicarbonates, hydroxides, hydrides, alkoxides, aryl amines, aliphatic amines, heterocyclic compound and like thereof.

In yet another embodiment of the present invention, the base is selected from the group consisting of NaOH, KOH, $Na_2CO_3$, $NaHCO_3$, NaH, $NaOCH_3$, Aryl-$NH_2$ and mixture thereof.

In still another embodiment of the present invention, solvent used is selected from group consisting of esters, ketones, aliphatic or aromatic hydrocarbons, acids, nitriles, water, aldehydes, alcohols, halides, non-polar solvents and mixture thereof.

In still another embodiment of the present invention, solvent used is selected from the group consisting of toluene, methanol, ethanol, acetonitrile, THF, acetone, petroleum ether, n-hexane, isopropanol, acetic acid, ethyl acetate, dichloromethane, water, water miscible solvents and mixtures thereof.

In still another embodiment of the present invention, enantio-purity of the said Lacosamide (R)-1 is >98% ee and yield is in the range of 40 to 50%.

DETAILED DESCRIPTION OF THE INVENTION

Figure 1:
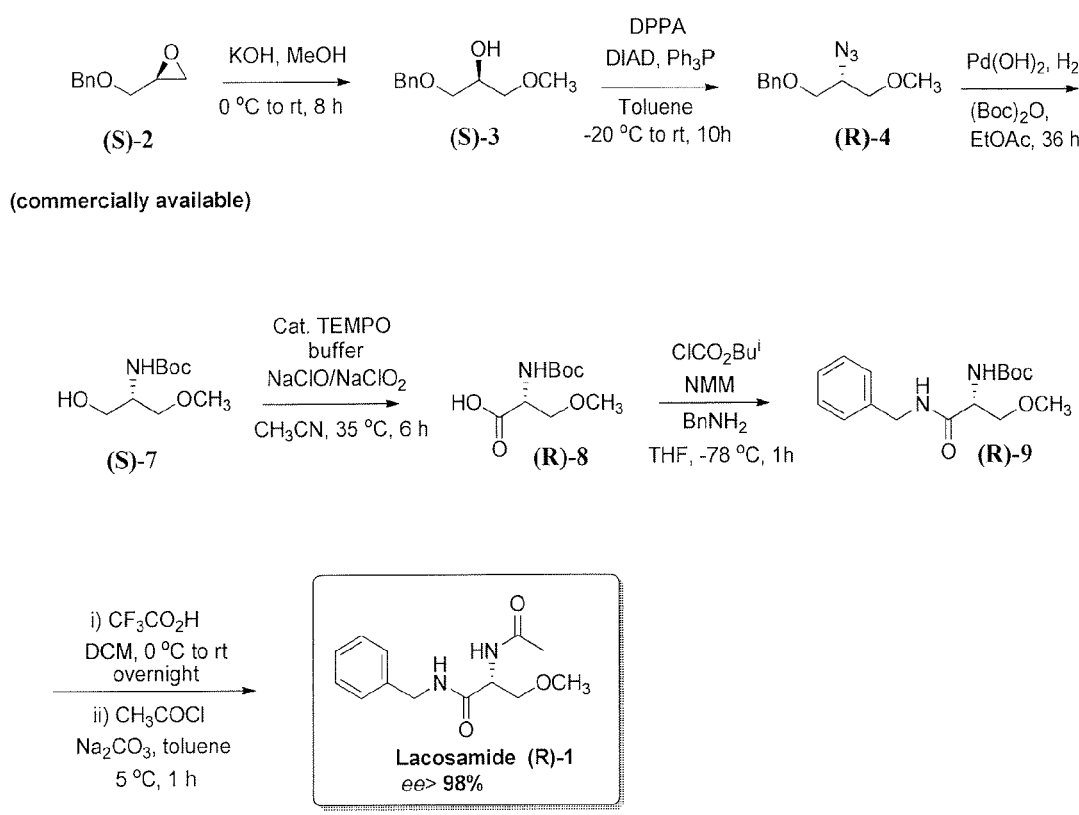
FIG. 1 is a Scheme 1 representing synthesis of (R)-Lacosamide (R)-1 from (S)-benzyl glycidyl ether (S)-2.
Figure 2:
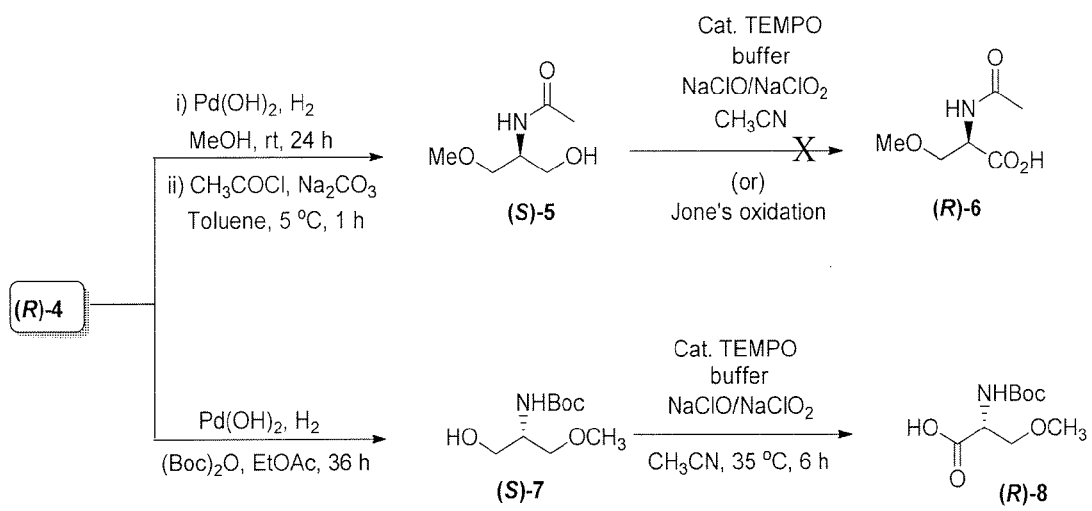
FIG. 2 is a Scheme 2 representing synthesis of N-substituted methoxy propanoic acid compound (R)-8.

The present invention relates to cost effective, efficient and improved process for the synthesis of R-Lacosamide from (S)-benzyl glycidyl ether in high enantiopurity (>98% ee) and over all 40-50% yield by using readily available starting materials.

In an aspect, the present invention provides a novel synthesis of R-Lacosamide (Scheme-1) comprises the following steps:
  a. regioselective ring opening of (S)-benzyl glycidyl ether (S)-2 to form corresponding sec-alcohol (S)-3;
  b. preparing azido derivative (R)-4 from sec-alcohol (S)-3 under Mitsunobu condition;

c. catalytic hydrogenating/hydrogenolysis and concomitant protection of (R)-4, to obtain (S)-7;

d. oxidizing (S)-7 into an acid (R)-8 using cat TEMPO/bleach condition;

e. subsequent coupling of (R)-8 with benzyl amine (BnNH$_2$), using mixed anhydride method to obtain (R)-9; and f. deprotecting followed by N-acetylation of (R)-9 in suitable condition to afford Lacosamide (R)-1 in high enantiopurity and yield.

The present invention provides synthesis of key intermediate compound (R)-4, which is commenced with the readily available starting material (S)-benzyl glycidyl ether (S)-2. Moreover, the regioselective ring opening of (S)-benzyl glycidyl ether (S)-2 with alcohol selected from the group consist of C1-C5 alcohol, branched alcohol, diol, triol, aryl alcohol and mixture thereof; preferably, C1-C5-alcohols and in the presence of a base, to give the corresponding secondary alcohol (S)-3 with the yield nearly about 98%, at about 0° C. to 40° C. in 7-10 hrs.

Further the suitable base for the epoxide opening reaction (regioselective ring opening) is selected from metal hydrides, hydroxides, oxides, carbonates, bicarbonates, alkoxides; preferably NaOH, KOH, Ca(OH)$_2$, (Na$_2$CO$_3$), NaHCO$_3$, NaOCH$_3$; whereas solvents used in the reaction mixture are selected from water, esters, ethers, hydrocarbons, alcohols, ketones, unsaturated hydrocarbons, acids, non-polar solvents and mixture thereof.

The secondary alcohol (S)-3 is subsequently converted in to the desired azido derivative (R)-4 in 80-90% yield using DPPA under Mitsunobu condition.

The azido compound (R)-4 is subjected to Pd(OH)$_2$ catalyzed hydrogenation/hydrogenolysis followed by N-acetylation using acetylating agent under basic condition can be afforded the compound (S)-5 in 80-90% yield (Scheme-2). Further the obtained compound (S)-5 may be converted into an acid (R)-6, followed by coupling with benzylamine to complete the synthesis of Lacosamide 1.

However, the oxidation of compound (S)-5 to acid (R)-6 is posed a problem, wherein the suitable oxidative conditions viz. sodium chlorite catalyzed by TEMPO & bleach and Jones oxidative conditions (CrO3 in dil H$_2$SO$_4$ and acetone) are failed to produce the desired acid (R)-6.

To circumvent this problem, the present inventors have developed an alternate strategy by converting the azido compound (R)-4 into protected amino alcohol (S)-7, wherein the protecting groups are selected from Boc, Cbz, Tos, Fmoc, preferably Boc; followed by oxidation to get the acid (R)-8. Accordingly, the azido compound (R)-4 is subjected to catalytic hydrogenation/hydrogenolysis and concomitant protection with (Boc)$_2$O in suitable solvent, which subsequently afforded the N-Boc protected amino alcohol (S)-7 in 80-90% yield. The catalytic or catalytic transfer hydrogenation is carried out in presence of H$_2$ gas and catalyst selected from Pd/C, Pt/C, (Raney Ni), Rh/C, Platinum oxide, Pd(OH)$_2$/C, Lithium aluminium hydride, ammonium formate or mixture thereof.

Furthermore, the compound (S)-7 undergoes oxidation very smoothly, under sodium chlorite catalyzed by TEMPO & bleach in acetonitrile-phosphate buffer (pH in between 6.0 to 7.0) in presence of suitable solvent, that affords the corresponding acid R-8 in 80-90% yield. The acid (R)-8 is converted into the amide (R)-9 by coupling with benzylamine using mixed anhydride procedure (Scheme 1). The mixed anhydride method consists of two stages the first stage involves activating the carboxyl group of an N-α-protected amino acid with an appropriate alkyl chlorocarbonate, such as ethylchlorocarbonate or preferably isobutylchlorocarbonate, wherein the activation occurs in an organic solvent in the presence of a tertiary base. The second stage involves reacting the carbonic anhydride with a free amine component of an amino acid. The racemization of the anhydride derivative as a result of the strong activation of the carbonyl group can be reduced by employing protecting groups, such as Cbz or t-Boc, Furthermore, as a result of high reactivity, mixed carbonic anhydrides are prone to the formation of 5(4H)-oxazolones urethanes, diacyimides, esters and are subject to disproportion. Moreover high temperatures, prolonged activation times (the time interval between the addition to the alkylchlorocarbonate and the amine component after the mixed anhydride is formed), steric bulk of the amine component, and incomplete formation of the mixed anhydride such conditions render the unwanted side chain reactions.

To minimize the formation of oxazolone and urethane derivatives, the present inventors have carried out benzylamine coupling reaction of Boc-N-α-protected amino acid i.e. (R)-8 in presence of dried organic solvents such as ethyl acetate, tetrahydrofuran, t-butanol, or acetonitrile accompanied by tertiary base such as N-methyl morpholine at low temperature ranges from (−)60 to (−)90° C., which affords (R)-9 with yield 90-95%. The compound (R)-9 is finally, subjected to Boc-deprotection followed by N-acetylation using suitable acetylating agent in the presence of base that completes the synthesis of Lacosamide 1, in excellent enantioselectivity (>98% ee) and better yield (40 to 50%), wherein the structure of Lacosamide 1 is confirmed by its IR, $^1$H NMR, $^{13}$C NMR and mass spectral analysis.

The acetylating agent is selected from one or more of acetic anhydride, acetyl chloride, acetic acid and mixture thereof or suitable derivatives thereof, whereas bases are not limited to the group consisting of NaOH, KOH, Na$_2$CO$_3$, NaOCH$_3$ and like and mixture thereof.

The pure (R)-Lacosamide or its salt obtained by the process of the present invention may be formulated into different dosage forms such as tablets, pills, powders, capsules, injections, granules, suspension, syrup, liquid, microemulsion, topical creams, ointments, suppositories, sachets, troches and lozenges etc comprising pharmaceutically acceptable excipients.

EXAMPLES

The following examples are given by way of illustration therefore should not be construed to limit the scope of the present invention.

General

Solvents were purified and dried by standard procedures prior to use. IR spectra were obtained from Perkin-Elmer Spectrum one spectrophotometer. $^1$H NMR and $^{13}$C NMR spectra were recorded on a Bruker AC-200 NMR spectrometer. Spectra were obtained in CDCl$_3$. Monitoring of reactions was carried out using TLC plates Merck Silica Gel 60 F254 and visualization with UV light (254 and 365 nm), I$_2$ and anisaldehyde in ethanol as development reagents. Optical rotations were measured with a JASCO P 1020 digital polarimeter. Mass spectra were recorded at ionization energy 70 eV on API Q Star Pulsar spectrometer using electrospray ionization. Enantiomeric excess was determined by chiral HPLC.

Example-1

Preparation of (S)-1-(Benzyloxy)-3-methoxypropan-2-ol (S)-3

To a stirred solution of (S)-benzyl glycidyl ether (S)-2 (4 g, 24.3 mmol) in methanol (40 mL) was added slowly a powdered KOH (4 g; 70 mmol) at 10° C. and the reaction mixture was stirred at 30° C. temperature for 8 h, after which the solvent was evaporated under reduced pressure. The residue was dissolved in ethylacetate (50 mL), washed with water, dried over $Na_2SO_4$, and evaporated under reduced pressure. The crude product was purified by column chromatography (silica gel, petroleum ether/acetone, 90:10) to afford (S)-1-(benzyloxy)-3-methoxypropan-2-ol (S)-3 as a colorless oil (4.6 g, 98%).

$[\alpha]^{25}_D$=−1.97 (c 1.55, EtOH) {lit. $[\alpha]^{25}_D$=−1.3 (c 1.54, EtOH)}; IR ($CHCl_3$, $cm^{-1}$): $v_{max}$ 3686, 3444, 3020, 2401, 1603, 1523, 1473, 1422, 1120, 1045, 758, 669; $^1$H NMR (200 MHz, $CDCl_3$): $\delta_H$ 3.38 (s, 3H), 3.43-3.47 (dd, J=5.3, 3.4 Hz, 2H), 3.50-3.55 (dd, J=5.8, 3.1 Hz, 2H), 3.94-4.04 (m, 1H), 4.56 (s, 2H), 7.29-7.41 (m, 5H); $^{13}$C NMR (50 MHz, $CDCl_3$): $\delta_C$ 137.9 (C), 128.4 (CH, 2 carbons), 127.7 (CH, 3 carbons), 73.8 ($CH_2$), 73.4 ($CH_2$), 71.3 ($CH_2$), 69.4 (CH), 59.2 ($CH_3$); MS: m/z 219 [M+Na]$^+$.

Example 2

Preparation of (R)-((2-azido-3-methoxypropoxy)methyl)benzene (R)-4

A solution of Diisopropyl azodicarboxylate (DIAD) (3.1 mL, 15.9 mmol) in dry toluene (5 mL) was added dropwise to a solution of (S)-3 (2.5 g, 13.2 mmol) and triphenylphosphine (4.1 g, 15.9 mmol) in dry toluene (50 mL) under $N_2$ atmosphere at 0° C. After 15 min, diphenylphosphoryl azide (3.6 mL, 15.9 mmol) was added drop wise and the reaction mixture was stirred at 25° C. temperature for 10 h. Solvent was removed under reduced pressure and the residue was purified by column chromatography (silica gel, petroleum ether/ethyl acetate, 95:05) to yield (R)-4 as colorless oil (2.4 g, 83%).

$[\alpha]^{25}_D$=+8.3 (c 2, $CHCl_3$); IR ($CHCl_3$, $cm^{-1}$): $v_{max}$ 3392, 2969, 2878, 1661, 1542, 1463, 1441, 1384, 1289, 1073, 1017, 988, 930, 756, 667; $^1$H NMR (200 MHz, $CDCl_3$): $\delta_H$ 3.37 (s, 3H), 3.46-3.52 (dd, J=5.4, 3.7 Hz, 2H), 3.54-3.61 (m, 2H), 3.68-3.79 (m, 1H), 4.56 (s, 2H), 7.28-7.37 (m, 5H); $^{13}$C NMR (50 MHz, $CDCl_3$): $\delta_C$ 137.7 (C), 128.5 (CH, 2 carbons), 127.8 (CH), 127.7 (CH, 2 carbons), 73.5 ($CH_2$), 72.2 ($CH_2$), 69.8 ($CH_2$), 60.6 (CH), 59.2 ($CH_3$); MS: m/z 244 [M+Na]$^+$; Anal. Calcd for $C_{11}H_{15}N_3O_2$: C, 59.71; H, 6.83; N, 18.99. Found: C, 59.43; H, 7.11; N, 19.20.

Example 3

Preparation of (S)-tert-butyl 1-hydroxy-3-methoxypropan-2-ylcarbamate (S)-7

To a solution of (R)-4 (2.0 g, 9 mmol) and $Boc_2O$ (2.1 g, 10 mmol) in ethyl acetate (30 mL) was added palladium hydroxide on activated charcoal (200 mg, 10-20 wt %) and the reaction mixture was stirred under hydrogen (60 psi) for 36 h. After completion of the reaction (indicated by TLC), filtered the catalyst over a plug of celite bed (EtOAc eluent) and the solvent was evaporated under reduced pressure. The crude product was purified by column chromatography (silica gel, petroleum ether/acetone, 80:20) to yield (S)-7 as colorless oil (1.6 g, 86%).

$[\alpha]^{25}_D$=+3.8 (c 0.95, $CHCl_3$) {lit. $[\alpha]^{25}_D$=+26.4 (c 0.995, $CHCl_3$)}; IR ($CHCl_3$, $cm^{-1}$): $v_{max}$ 3683, 3443, 3018, 2981, 2898, 1703, 1504, 1393, 1368, 1169, 1092, 928, 848, 669; $^1$H NMR (200 MHz, $CDCl_3$): $\delta_H$ 1.45 (s, 9H), 2.94 (bs, 1H), 3.37 (s, 3H), 3.52-3.56 (apparent t, J=3.7 Hz, 2H), 3.61-3.80 (m, 2H), 5.20 (m, 1H); $^{13}$C NMR (50 MHz, $CDCl_3$): $\delta_C$ 156.1 (CO), 79.2 (C), 73.1 ($CH_2$), 63.8 ($CH_2$), 59.2 (CH), 51.4 ($CH_3$), 28.3 ($CH_3$, 3 carbons); MS: m/z 228 [M+Na]$^+$.

Example-4

Synthesis of (R)-2-(tert-butoxycarbonylamino)-3-methoxypropanoic Acid (R)-8

A mixture of (S)-7 (1 g, 4.9 mmol), TEMPO (0.05 g, 0.32 mmol), acetonitrile (20 mL), and sodium phosphate buffer (16 mL, 0.67 M, pH 6.7) was heated to 35° C. Then sodium chlorite (1.32 g dissolved in 2 mL water, 14.6 mmol) and dilute bleach (4-6%, 1 mL diluted in 2 mL water) were added simultaneously over 1 h. The reaction mixture was stirred at 35° C. until the reaction is complete (6 h, TLC), then cooled to room temperature. Water (30 mL) was added and the pH was adjusted to 8 with 2 N NaOH. The reaction was quenched by pouring into ice cold $Na_2SO_3$ solution maintained at <20° C. After stirring for 30 min at 30° C. ethylacetate (30 mL) was added and continued the stirring for additional 15 min. The organic layer was separated and discarded. More ethylacetate (30 mL) was added, and the aqueous layer was acidified with 2N HCl to pH 3. The organic layer was separated, washed with water (2×15 mL), brine (20 mL) and concentrated under reduced pressure to afford the carboxylic acid (R)-8 (0.88 g, 83%).

$[\alpha]^{25}_D$=−19.2 (c 1.4, $CHCl_3$); IR ($CHCl_3$, $cm^{-1}$): $v_{max}$ 3443, 3019, 2982, 2932, 1708, 1501, 1393, 1369, 1216, 1164, 1119, 1064, 927, 757, 669; $^1$H NMR (200 MHz, $CDCl_3$): $\delta_H$ 1.46 (s, 9H), 3.38 (s, 3H), 3.59-3.66 (dd, J=9.4, 3.7 Hz, 1H), 3.84-3.90 (dd, J=9.6, 3.1 Hz, 1H), 4.41-4.47 (m, 1H), 5.42 (d, J=8.2 Hz, 1H) 8.16 (bs, 1H); $^{13}$C NMR (50 MHz, $CDCl_3$): $\delta_C$ 175.4 (CO), 155.8 (CO), 80.3 (C), 72.1 ($CH_2$), 59.3 (CH), 53.7 ($CH_3$), 28.3 ($CH_3$, 3 carbons); MS: m/z 242 [M+Na]$^+$.

Example-5

Synthesis of (R)-tert-butyl 1-(benzylamino)-3-methoxy-1-oxopropan-2-ylcarbamate (R)-9

To a solution of acid (R)-8 (0.7 g, 3.2 mmol) in dry THF was added N-methylmorpholine (0.43 mL, 3.8 mmol) at −78° C. under argon atmosphere. After 5 min, isobutyl chloroformate (0.5 mL, 3.8 mmol) was added and stirred the content for another 5 min. To this reaction mixture benzylamine (0.4 mL, 3.8 mmol) was added at −78° C. and allowed the reaction mixture to stir at 30° C. for 1 h. After completion of the reaction, reaction mixture was filtered, washed with ethylacetate. The solvent was removed under reduced pressure and the crude product was subjected to column chromatography (silica gel, petroleum ether/acetone, 85:15) to yield (R)-9 as colorless solid (0.9 g, 90%).

m.p 63-64° C.; $[\alpha]^{25}_D$=−20.5 (c 0.9, $CHCl_3$); IR ($CHCl_3$, $cm^{-1}$): $v_{max}$ 3683, 3431, 3020, 2931, 2401, 1714, 1523, 1496, 1368, 1165, 1119, 928, 758, 669; $^1$H NMR (200 MHz, $CDCl_3$): $\delta_H$ 1.43 (s, 9H), 3.37 (s, 3H), 3.47-3.54 (dd, J=9.2, 6.1 Hz, 1H), 3.82 (dd, J=9.3, 3.7 Hz, 1H), 4.27 (m, 1H), 4.47 (d, J=5.1 Hz, 1H), 5.41 (bs, 1H), 6.77 (m, 1H), 7.22-7.37 (m, 5H); $^{13}$C NMR (50 MHz, $CDCl_3$): $\delta_C$ 170.3 (CO), 155.5 (CO), 137.9 (C), 128.7 (CH, 2 carbons), 127.5 (CH, 3 carbons), 80.4 (C), 72.1 ($CH_2$), 59.1 ($CH_3$), 54.0 (CH), 43.5 ($CH_2$), 28.3 ($CH_3$, 3 carbons); MS: m/z 331 [M+Na]$^+$.

Example-6

Preparation of (R)-2-acetamido-N-benzyl-3-methoxypropanamide (R)-1 (Lacosamide)

To a solution of compound (R)-9 (0.6 g, 1.9 mmol) in dichloromethane (7 mL) was added trifluoroacetic acid (3 mL) and the reaction mixture was stirred at 30° C. overnight (12 h), after which the solvent was evaporated under reduced pressure. Subsequently, the residue was dissolved in dry toluene and added Na$_2$CO$_3$ (0.6 g, 5.7 mmol). The reaction mixture was cooled to 0° C. and acetylchloride (0.14 mL, 2.0 mmol) was added slowly and stirred the content at 5° C. for 1 h. After completion of the reaction, filtered the solid and the solvent was evaporated under reduced pressure. The crude product was purified by column chromatography (silica gel, dichloromethane/methanol, 95:05) to afford (R)-1 (Lacosamide) as a colorless solid (0.38 g, 80%).

m.p 139-40° C. (Lit 143-44° C.); [α]$_D$: +16.1 (c 1, MeOH) {Lit. +16.4 (c 1, MeOH)}; IR (CHCl$_3$): γ 3685, 3421, 3020, 1663, 1523, 1426, 1118, 1030, 929 cm$^{-1}$; $^1$H NMR (400 MHz, CDCl$_3$): δ 2.05 (s, 3H, COCH$_3$), 3.40 (s, 3H, OCH$_3$), 3.45 (apparent t, J=9.7, 8.0 Hz, 1H, OCH$_2$), 3.83 (dd, J=9.4, 3.4 Hz, 1H, OCH$_2$), 4.50 (d, J=4.5 Hz, 2H, CH$_2$Ph), 4.52-4.58 (m, 1H), 6.48 (bs, 1H, NH), 6.78 (bs, 1H, NH), 7.26-7.38 (m, 5H, Ph); $^{13}$C NMR (50 MHz, CDCl$_3$): δ 170.7 (CO), 170.0 (CO), 137.7 (C), 128.6 (CH, 2 carbons), 127.4 (CH, 3 carbons), 71.8 (CH$_2$), 59.1 (CH$_3$), 52.6 (CH), 43.6 (CH$_2$), 23.2 (CH$_3$); MS: m/z 273 [M+Na]$^+$; (ee 98.3%) ee >98% [The ee of 1 was determined by chiral HPLC analysis; Chiralcel OD-H (250×4.6 mm) column; eluent: pet.ether/isopropanol/ trifluoroacetic acid (60:40:0.1); flow rate 0.5 mL/min; detector: 220 nm [(R)-isomer t$_R$=10.43 min; (S)-isomer t$_R$=11.8 min].

Advantages of the Invention

1. The process uses commercially available starting material, namely (S)-benzyl glycidyl ether.
2. The process results in very high enantiopurity of Lacosamide (ee >98%).
3. The overall yield of the process is 40-50%.
4. The present process avoids cumbersome O-methylation step used in prior art (in earlier methods, this step involves expensive silver oxide, longer reaction period (3-4 days), and partial racemization).

What is claimed:

1. A process for synthesis of >98% ee enantio-pure Lacosamide (R)-1 from (S)-benzyl glycidyl ether and the said process comprising the steps of:

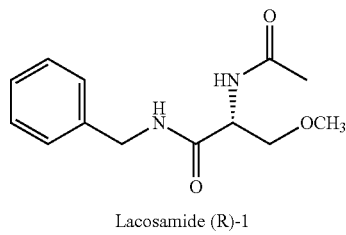 [SMILES: COC[C@@H](NC(C)=O)C(=O)NCc1ccccc1]

Lacosamide (R)-1 i. regioselective ring opening of compound (S)-benzyl glycidyl ether (S)-2 in presence of base and alcohol at temperature in the range of 0 to 60° C. for period in the range of 7 to 10 h to obtain corresponding sec-alcohol (S)-3;

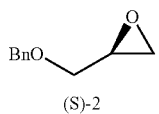 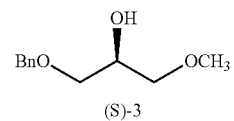

ii. preparing azido derivative (R)-4 from sec-alcohol (S)-3 under Mitsunobu condition;

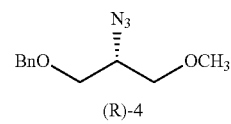 [SMILES: COC[C@H](COCc1ccccc1)N=[N+]=[N-]]

iii. catalytical hydrogenation, hydrogenolysis and concomitant protection of (R)-4 as obtained in step (ii) by using protecting group in solvent to obtain compound (S)-7;

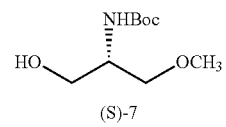

iv. oxidizing (S)-7 as obtained in step (iii) in presence of (2,2,6,6-Tetramethylpiperidin-1-yl)oxyl (TEMPO) and bleach in acetonitrile-phosphate buffer of pH in the range of 6.0 to 7.0 in solvent to obtain (R)-8;

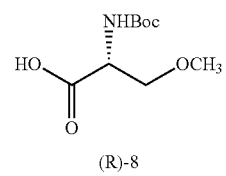 [SMILES: COC[C@@H](NC(=O)OC(C)(C)C)C(=O)O]

v. subsequent coupling of (R)-8 as obtained in step (iv) with benzyl amine using mixed anhydride method to obtain (R)-9;

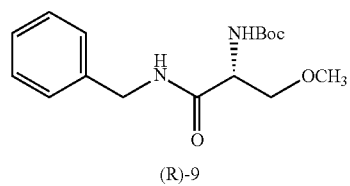 [SMILES: COC[C@@H](NC(=O)OC(C)(C)C)C(=O)NCc1ccccc1]

vi. deprotecting (R)-9 as obtained in step (iv) and (v) followed by N-acetylation in presence of acetylating agent, base and solvent to obtain Lacosamide (R)-1.

2. The process as claimed in step (i) of claim 1, wherein the base is selected from the group consisting of metal hydrides, hydroxides, oxides, carbonates, bicarbonates, alkoxides or primary and secondary amine, ammonia, alkyl amine; preferably NaOH, KOH, Na$_2$CO$_3$, NaHCO$_3$, NaOCH$_3$.

3. The process as claimed in step (i) of claim 1, wherein the alcohol is selected from the group consisting of (C1-C5) alcohol, branched alcohol, diol, triol, aryl alcohol; preferably, C1-C5-alcohols.

4. The process as claimed in step (ii) of claim 1, wherein the temperature is maintained in the range between −20° C. to 60° C. preferably −20° to 40° C.

5. The process as claimed in step (iii) of claim 1, wherein catalytic hydrogenation is carried out in presence of $H_2$ and catalyst selected from the group consisting of Pd/C, Pt/C, Raney Ni, Rh/C, Platinum oxide, Pd(OH)$_2$/C, Lithium aluminium hydride, ammonium formate or mixture thereof.

6. The process as claimed in step (iii) of claim 1, wherein the protecting groups are selected from the group consisting of Boc, Cbz, Tos or Fmoc preferably Boc.

7. The process as claimed in step (v) of claim 1, wherein temperature in the range of (−) 60 to (−) 90° C. preferably (−) 70 to (−) 80° C.

8. The process as claimed in step (vi) of claim 1, wherein acetylating agent used is selected from the group consisting of acetic anhydride, acetyl chloride, acetic acid and mixture thereof or suitable derivatives thereof.

9. The process as claimed in step (vi) of claim 1, wherein the base is selected from the group consisting of carbonates, bicarbonates, hydroxides, hydrides, alkoxides, aryl amines, aliphatic amines, heterocyclic compound and like thereof.

10. The process according to claim 9, wherein the base is selected from the group consisting of NaOH, KOH, Na$_2$CO$_3$, NaHCO$_3$, NaH, NaOCH$_3$, Aryl-NH$_2$ and mixture thereof.

11. The process as claimed in step (vi) of claim 1, wherein solvent used is selected from group consisting of esters, ketones, aliphatic or aromatic hydrocarbons, acids, nitriles, water, aldehydes, alcohols, halides, non-polar solvents and mixture thereof.

12. The process as claimed in claim 11, wherein solvent used is selected from the group consisting of toluene, methanol, ethanol, acetonitrile, THF, acetone, petroleum ether, n-hexane, isopropanol, acetic acid, ethyl acetate, dichloromethane, water, water miscible solvents and mixtures thereof.

13. The process as claimed in claim 1, wherein yield of the said Lacosamide (R)-1 is in the range of 40 to 50%.

\* \* \* \* \*